United States Patent
Blasenheim et al.

(10) Patent No.: US 9,243,999 B2
(45) Date of Patent: *Jan. 26, 2016

(54) ELLIPSOMETER FOCUSING SYSTEM

(71) Applicant: Nanometrics Incorporated, Milpitas, CA (US)

(72) Inventors: Barry J. Blasenheim, San Jose, CA (US); Amit Shachaf, Palo Alto, CA (US)

(73) Assignee: Nanometrics Incorporated, Milpitas, CA (US)

(*) Notice: Subject to any disclaimer, the term of this patent is extended or adjusted under 35 U.S.C. 154(b) by 102 days.

This patent is subject to a terminal disclaimer.

(21) Appl. No.: 14/046,558

(22) Filed: Oct. 4, 2013

(65) Prior Publication Data

US 2014/0098369 A1 Apr. 10, 2014

Related U.S. Application Data

(63) Continuation of application No. 13/082,300, filed on Apr. 7, 2011, now Pat. No. 8,559,008.

(51) Int. Cl.
*G01J 4/00* (2006.01)
*G01N 21/21* (2006.01)
*G02B 7/28* (2006.01)

(52) U.S. Cl.
CPC ............... *G01N 21/211* (2013.01); *G02B 7/28* (2013.01)

(58) Field of Classification Search
CPC . G01N 21/211; G01N 2021/213; G01J 3/447; G02B 7/28
See application file for complete search history.

(56) References Cited

U.S. PATENT DOCUMENTS

| | | | | |
|---|---|---|---|---|
| 4,129,775 A | * | 12/1978 | O'Meara | 250/203.1 |
| 4,407,563 A | * | 10/1983 | Minott | 359/583 |
| 5,136,149 A | | 8/1992 | Fujiwara | |
| 5,608,526 A | | 3/1997 | Piwonka-Corle et al. | |
| 5,793,480 A | | 8/1998 | Lacey et al. | |

(Continued)

FOREIGN PATENT DOCUMENTS

WO   WO 2006/091781 A1   8/2006

OTHER PUBLICATIONS

Cao et al. (2007). "System error removal and structure optimization based on Fizeau interferometer," *Optik* vol. 118(10):495-501.

(Continued)

*Primary Examiner* — Kara E Geisel
(74) *Attorney, Agent, or Firm* — Silicon Valley Patent Group LLP

(57) ABSTRACT

An ellipsometer includes an integrated focusing system with a beam splitter between the sample and the ellipsometer detector. The beam splitter provides a portion of the radiation to a lens system that magnifies any deviation from a best focus position by at least 2×. The focusing system includes a 2D sensor, where the spot of light focused on the sensor is 50 percent or smaller than the sensor. The focusing system may further include a compensator to correct optical aberrations caused by the beam splitter. A processor receives an image signal and finds the location of the spot from which focus error can be determined and used to correct the focal position of the ellipsometer. The processor compensates for movement of the spot caused by rotating optics. Additionally, a proportional-integral-derivative controller may be used to control exposure time and/or gain of the camera.

20 Claims, 3 Drawing Sheets

(56) References Cited

U.S. PATENT DOCUMENTS

| | | | |
|---|---|---|---|
| 6,469,788 | B2 | 10/2002 | Boyd et al. |
| 6,687,002 | B2 | 2/2004 | Stehle et al. |
| 6,738,138 | B2 | 5/2004 | Wei |
| 8,559,008 | B2 | 10/2013 | Blasenheim et al. |
| 2002/0024668 | A1 | 2/2002 | Stehle et al. |
| 2005/0174575 | A1 | 8/2005 | Norton et al. |
| 2008/0225661 | A1* | 9/2008 | El Husseini et al. ....... 369/53.17 |
| 2009/0059228 | A1 | 3/2009 | Horie |
| 2009/0066953 | A1 | 3/2009 | Horie |
| 2010/0085576 | A1* | 4/2010 | Norton et al. .................. 356/521 |
| 2011/0051132 | A1 | 3/2011 | Petrenko et al. |

OTHER PUBLICATIONS

Ma et al. (May 11, 2009). "Error analysis of CCD-based point source centroid computation under the background light," *Optics Express* vol. 17(10):8525-8541.

Invitation to Pay Additional Fees and Communication Relating to the Results of the Partial International Search mailed on Jun. 27, 2012 for PCT Application PCT/US2012/031222 filed on Mar. 29, 2012, 9 pages.

International Search Report and Written Opinion mailed on Sep. 26, 2012 for PCT Application PCT/US2012/031222 filed on Mar. 29, 2012, 17 pages.

International Preliminary Report on Patentability mailed on Oct. 17, 2013 for PCT Application PCT/US2012/031222 filed on Mar. 29, 2012, 12 pages.

Office Action mailed on for Dec. 18, 2012 for U.S. Appl. No. 13/082,300, filed Apr. 7, 2011, 7 pages.

Response to Office Action mailed on Mar. 18, 2013 for U.S. Appl. No. 13/082,300, filed Apr. 7, 2011, 15 pages.

Notice of Allowance mailed on Jun. 11, 2013 for U.S. Appl. No. 13/082,300, filed Apr. 7, 2011, 9 pages.

* cited by examiner

ELLIPSOMETER FOCUSING SYSTEM

CROSS-REFERENCE TO RELATED APPLICATION(S)

This application is a continuation of U.S. Ser. No. 13/082,300, filed Apr. 7, 2011, which is assigned to the assignee hereof and which is incorporated herein by reference.

BACKGROUND

Ellipsometers are optical metrology devices that detect changes in the polarization state of light reflected from a surface of a sample in order to measure characteristics of the sample. By way of example, FIG. 1 illustrates a conventional spectroscopic ellipsometer 10 that includes a broad band light source 12, a polarizer 14 and lens 15 to focus the illuminating light on the surface of a sample 16 that is positioned on a stage 18. The ellipsometer 10 further includes an analyzer 22 after passing through lens 20. After passing through analyzer 22, the reflected light is focused by lens system 24 on a detector 26.

The ellipsometer 10 must be properly focused on the sample. Some systems use independent focusing systems, i.e., systems that attached to the ellipsometer, but that use an independent light path to determine the position of the focusing system, and thus, the ellipsometer, with respect to the sample. Such focusing systems, however, require very precise alignment, which is expensive and difficult. FIG. 1 illustrates example of an integrated focusing system that includes a mirror 28 with an aperture 30. The mirror 28 reflects the outside rays of the reflected beam to a focus detector 32, while the inner rays of the reflected beam are transmitted through the aperture 30 and received by the ellipsometer detector 26. Typically, the focus detector 32 is a position sensitive device (PSD) or a "quad cell", neither of which image the detected light but, in principle, sums all of the light that is received. Accordingly, such devices are susceptible to inaccuracies due to stray light. Other systems, such as that described in U.S. Pat. No. 5,608,526, use a camera as the focus detector 32. Nevertheless, such a system still suffers from imprecision due to systematic errors caused by the mirror 28, because only the outer part of the beam is sampled by detector 32. Moreover, a focus system, such as that described in U.S. Pat. No. 5,608, 526, lack the precision required to produce a small illuminating spot size on the sample.

Accordingly, an improved focusing system for ellipsometers is desired.

SUMMARY

An ellipsometer includes an integrated focusing system that includes a beam splitter in the beam path between the sample and the ellipsometer detector. The beam splitter provides a portion of the radiation to a lens system that magnifies any deviation from a best focus position by at least 2×. The focusing system further includes a two-dimensional sensor, where the spot of light focused on the sensor is 50 percent or smaller than the sensor. The focusing system may further include a compensator positioned between the beam splitter and the detector to corrects optical aberrations caused by the beam splitter. A processor receives an image signal and finds the location of the spot. The deviation from the best focus position is determined using the location of the spot and the focal position of the ellipsometer is adjusted accordingly. The processor compensates for movement of the spot caused by rotating optics. Additionally, a proportional-integral-derivative controller may be used to control exposure time and/or gain of the camera.

DETAILED DESCRIPTION

Figure 2:
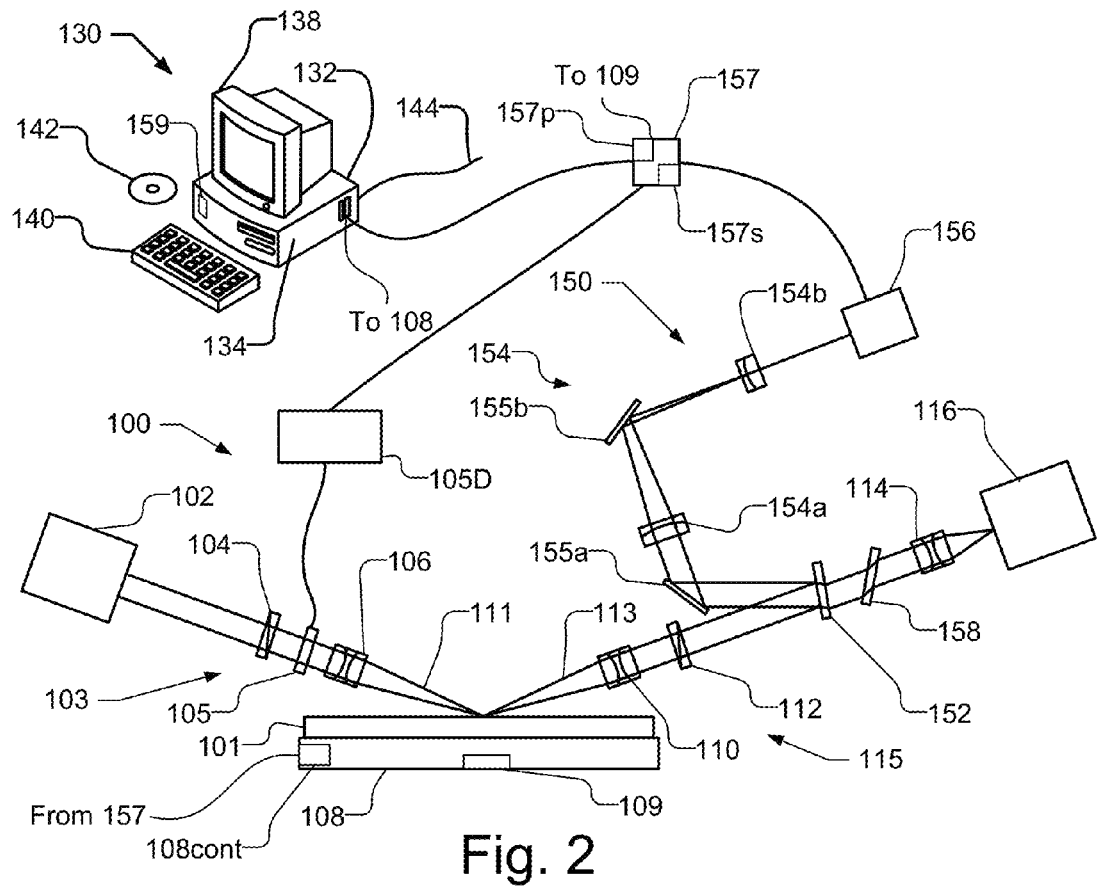
FIG. 2 illustrates an ellipsometer 100 with a high precision focusing system in accordance with an embodiment of the present invention.

FIG. 2 illustrates an ellipsometer 100 with a high precision focusing system 150. Ellipsometer 100 is illustrated as including a light source 102 and a polarization state generator 103 with a polarizer 104 and a rotating compensator 105, as well as a lens system 106, which focuses the illuminating light 111 on the surface of a sample 101 that is positioned on a stage 108. Ellipsometer 100 may be monochromatic or spectroscopic. The incident illuminating light 111 has a known polarization state due to the polarizer 104 and rotating compensator. The polarization state of the light reflected by the sample 101 is analyzed by a polarization state analyzer 115, e.g., by passing the reflected light 113 through another polarizer 112, commonly referred to as analyzer 112, after passing through another lens system 110. After passing through the analyzer 112, the reflected light 113 is focused by a lens system 114 on a detector 116.

The ellipsometer 100 includes an integrated auto focusing system 150 that images the same light rays that are used by the ellipsometer 100 and additionally magnifies the deviation from a best focus position. Focusing system 150 includes a beam splitter 152 that directs a portion of the reflected light 113 to a lens system 154 that may include fold mirrors 155a, 155b if desired. The lens system 154 focuses the light onto a camera 156.

Figure 3:
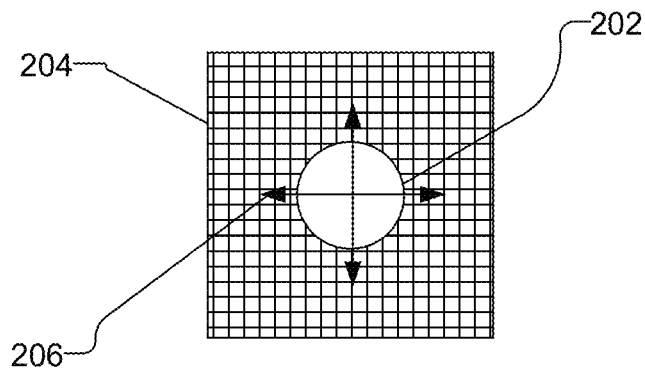
FIG. 3 illustrates a two-dimensional sensor of a camera in the focusing system with a significantly smaller light spot thereon.

As illustrated in FIG. 3, the lens system 154 focus the light into a spot 202 that is significantly smaller than the sensor 204 for the camera 156. The sensor 204 may be, e.g., a two dimensional sensor array such as a CCD. The spot 202 may be 1%-50%, e.g., 10% or less, of the size of the sensor 204, which increases the useful auto-focus range. The lenses of lens system 154, illustrated by lenses 154a and 154b in FIG. 2, are arranged to magnify the deviation from the best focus position thereby providing greater measurement precision. For example, as illustrated by arrow 206 in FIG. 3, the movement of the location of the spot 202 on the sensor 204 provides a magnified indication of the deviation from the best focus position. The size of the spot on the sensor 204 may change slightly as the sample 101 is scanned through the focal range, however, this is a relatively small effect to which the spot location calculation may be configured to be insensitive. The magnification produced by lens system 154 with respect to the deviation from the best focus position may be 2× to 5× or greater, such as 10×. However, reduction of spot size decreases the focus precision and, thus, a trade-off between auto focus range and precision is made, as smaller spot makes the spot location calculation less precise but provides a higher spot intensity. Accordingly, if desired, a large spot, e.g., the size of the sensor 204 may be produced, which may be used to provide a more accurate spot location calculation.

Figure 1:
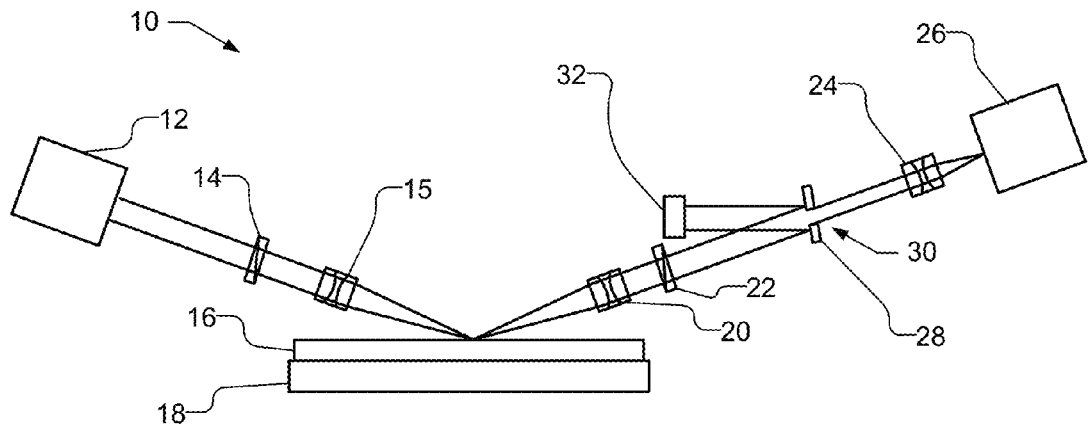
FIG. 1 illustrates an ellipsometer with a conventional focusing system.

As illustrated in FIG. 2, the beam splitter 152 of the focusing system 150 reflects a portion of the reflected light 113, e.g., 4% to 10% of the total light intensity, to the focusing system 150, and transmits the remaining portion of the reflected light 113, e.g., 90% or more of the total light intensity, to the ellipsometer detector 116. In the configuration illustrated in FIG. 2, the reflected portion is provided to the focusing system 150, but if desired, the transmitted portion of the reflected light 113 may be provided to the focusing system 150, where 4% to 10% of the reflected light intensity is transmitted. The use of beam splitter 152, which is sometimes referred to as a "pick off" beam splitter, is advantageous as the entire cross section of the reflected light 113 beam is sampled by the focusing system 150, as opposed to the system shown in FIG. 1, in which only the outside rays of the reflected light are used. By sampling the entire beam of the reflected light 113, the focusing system 150 is insensitive to systematic errors caused by sampling only portions of the reflected light 113.

The beam splitter 152 will produce some optical aberrations in the reflected light 113. Accordingly, if the aberrations from beam splitter 152 are too high, a compensator 158 may be used between the beam splitter 152 and the detector 116. The compensator 158 is configured to correct, e.g., eliminate or reduce, the aberrations caused by the beam splitter 152. With the use of an appropriately configured compensator 158, optical aberrations in the ellipsometer 100 may be very low, thereby enabling the measurement of the sample 101 using a small spot size, e.g., less than 100 μm.

As illustrated in FIG. 2, the camera 156 for the focus system 150 is coupled to a computer 130, e.g., through a frame grabber board 157. The rotating compensator 105 and stage 108 may also be connected to the frame grabber board 157 directly or through controller/drivers (105D). If desired, the detector 116 for the ellipsometer 100 may be coupled to the same computer 130 or a different computer. The computer 130 includes a processor 132 with memory 134, as well as a user interface including e.g., a display 138 and input devices 140. The frame grabber board 157 includes a processor 157$p$, (which may be a field programmable gate array (FPGA)) that is configured to determine a focus error, which is used to control the focus position of the stage 108, e.g., via a stage servo controller 108$cont$ that receives focus error data from the frame grabber board 157 and controls an actuator 109 in the stage 108 accordingly. Thus, in one embodiment, the frame grabber board 157 is processing the focus error directly from the camera 156 and providing the focus adjustment to the stage servo controller 108$cont$ without input from the computer 130. Of course, if desired, computer 130 may be used in part or all of the processing of the focus error and instructing the stage servo controller 108$cont$. It should be understood that a processor, such as processor 157$p$ on frame grabber board 157, may include one or more separate processing units, e.g., processor 157$p$ may include a first processor for image processing and a separate processor for focus error determination. Additionally, one or more processors may be located in other positions, besides frame grabber board 157. For example, processor 157$p$ (or one or more of the processor units that comprise processor 157$p$) may be located in camera 156, or elsewhere.

If the processor 157$p$ is, e.g., a microprocessor, that carries out instructions of a computer program, the data structures and software code for automatically implementing one or more acts described in this detailed description can be implemented by one of ordinary skill in the art in light of the present disclosure and stored, e.g., on a computer readable storage medium 157$s$, which may be any device or medium that can store code and/or data for use by a computer system. The computer-usable storage medium 157$s$ may be, but is not limited to, magnetic and optical storage devices such as disk drives, magnetic tape, compact discs, and DVDs (digital versatile discs or digital video discs). A communication port may also be used to receive instructions that are used to program the processor 157$p$ to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described. For example, as discussed above, a field programmable gate array (FPGA) may be used. The FPGA may be either in the camera 156 or on a frame grabber board 157 internal or external to the computer 130. Where processor 157$p$ is an FPGA, computer readable storage medium 157$s$ may provide the programming file to embed the desired configuration in the processor 157$p$, which may be performed one time for a non-volatile FPGA, or otherwise at power-up. By avoiding the use of the main system CPU to perform the necessary calculations for auto focusing, the CPU is not slowed down. Further, a dedicated processor increases the image processing speed. Thus, the stage servo controller 108$cont$ may be directly coupled to the frame grabber board 157, which may provide a signal directly to the stage servo controller 108$cont$ through a Small Peripheral communication Interface (SPI) channel.

Most digital cameras, such as those used in conventional metrology systems include an internal auto exposure control. The auto exposure control of such cameras, however, is inadequate for the present high precision focusing system 150, which uses a single spot on the CCD. Auto exposure control in conventional cameras attempts to adjust the exposure for the whole CCD and thus will lose control when there is single spot on the CCD. Moreover, if the image is downloaded to the computer 130 to perform the exposure control, there would be too much delay, which would lead to unstable control. Thus, the focusing system 150 uses the camera exposure control I/O as a slave to the image processing dedicated processor, e.g., on the camera 156 or frame grabber board 157, so the exposure control is in good correlation to what is needed in the image processing. The exposure is adjusted with respect to only the spot on the CCD and not the entire CCD, which is, e.g., 99% empty. Thus, once the spot is located on the sensor 204, the exposure error based on the local intensity of the spot is calculated, as opposed to calculating the exposure error over the entire sensor. The exposure control I/O is set based on the exposure error calculation for the spot and is provided to a proportional-integral-derivative controller (PID) controller 159 in the frame grabber board 157 to predict the exposure time and/or gain for the camera 156 to create a stable exposure for the spot that follows the, e.g., 40 Hz sinusoidal, changes in the spot intensity.

Typically auto exposure algorithms require the acquisition of several images at several different exposure/gain settings to accurately calculate the correct exposure time/gain for the camera. As discussed above, however, the signal intensity is constantly changing as the rotating optic rotates, so the exposure time/gain would be constantly changing. Consequently, in a conventional system, the exposure time/gain for each desired exposure would have to be recalculated requiring the acquisition of several images at several different exposure time/gain settings to accurately calculate the correct exposure time/gain for each exposure. It is desirable to sample the auto focus signal as frequently as possible, and thus acquiring several images for each exposure would reduce the speed of the system. The PID controller 159, however, can calculate the next exposure time can be calculated to sufficient accuracy in real time so that the additional images are not necessary. The PID controller 159 may sample at about 40 times per cycle, enough to make a PID loop effective. The PID controller 159 may be on the FPGA processor 157p in the frame grabber board 157, which is performing the image processing, and thus, it may perform at full speed and sample every image if desired.

As is known in the art, an ellipsometer, such as ellipsometer 100, used to measure the properties and/or structures of a thin sample on a substrate vary the polarization state of the light going to the sample. There are a few standard ways of doing this, all of which are contemplated with the present disclosure. One way to vary the polarization state is to continuously rotate the polarizer 104 about the optical axis, while the analyzer 112, which transmits only one polarization state, is fixed. In this method, there is no need for rotating compensator 105. In the simplest case, where the sample does not change the polarization of the incident light, the result is a variation in the intensity of the light after the analyzer 112. For example, the analyzer 112 could be set to transmit only horizontally polarized light, and block vertically polarized light. With the polarizer 104 starting in a position in which the illuminating light 111 is horizontally polarized, the analyzer 112 would transmit 100% of the light. As the polarizer 104 rotates 90 degrees about the optical axis, the light is now vertically polarized. As a result, the analyzer 112 will block all of the light, and there will be no signal at the detector 116. As the polarizer moves another 90 degrees (180 degrees total) it is now transmitting horizontally polarized light again, and the analyzer would again transmit 100% of the light. A plot of the signal intensity vs. time, thus, produces a sine wave, where the intensity of the signal varies between 0% and 100% and the frequency of the sine wave is double the frequency of the rotation of the polarizer 104. Additionally, the analyzer 112 may rotate, while the polarizer 104 is held fixed. Alternatively, a rotating compensator 105, as illustrated in FIG. 2, may be used to vary the polarization state. The rotating compensator 105 will produce the same basic sinusoidal variation of intensity vs. time. Further, the rotating compensator 105 may be located on either side of the sample 101.

In use, a sample under test will change the polarization state of the incident light, which will change the intensity and phase of the resulting signal from the detector 116. Using the change in intensity and phase, the material properties of the sample 101 may be determined, which is the essence of ellipsometry and is well known in the art. However, changes in the intensity and phase also produce problems in an auto focus system for ellipsometers. When the intensity of the signal getting through the analyzer 112 drops to near zero, the auto focus camera 156 does not receive enough light to measure a spot location. This, in turn, creates problems with the auto focus system 150, because the servo control signal has vanished. Thus, the auto focus system 150 is configured to compensate for the periodic loss of an actuator control signal using filtering and interpolation to compensate for missing signal points.

The rotating compensator 105 (or polarizer 104) produces another problem for the auto focus system 150. In the ideal case, as the rotating optic (i.e., the compensator 105 or polarizer 104) rotates, the location of the illumination spot on the sample 101 does not move. However, the motor and bearings that rotate the rotating optic are not perfect, resulting in a wobble of the rotating optic. In addition, the input beam to the rotating optic and the output beam after the rotating optic will not be perfectly parallel. As a result of these two effects, the illumination spot on the sample 101 does move, which causes the spot to move on the two-dimensional sensor as the rotating optic rotates. The movement of the illumination spot in ellipsometer 100 is typically less than 2 μm, which despite being a small amount, is sufficient to cause problems for the auto focus system 150. Accordingly, the auto focus system 150 is configured to compensate for the movement of the illumination spot.

Additionally, some samples will scatter unwanted light into the path of the auto focus system 150. The amount and pattern of unwanted light will vary depending on the sample. While the optical system of the ellipsometer 100 may be designed to minimize receiving scattered light, the problem cannot be completely eliminated. If the unwanted or scattered light is not excluded from the spot location calculations of the auto focus system, errors will be produced. Accordingly, the auto focus system 150 is configured to be insensitive to scattered light.

Figure 4:
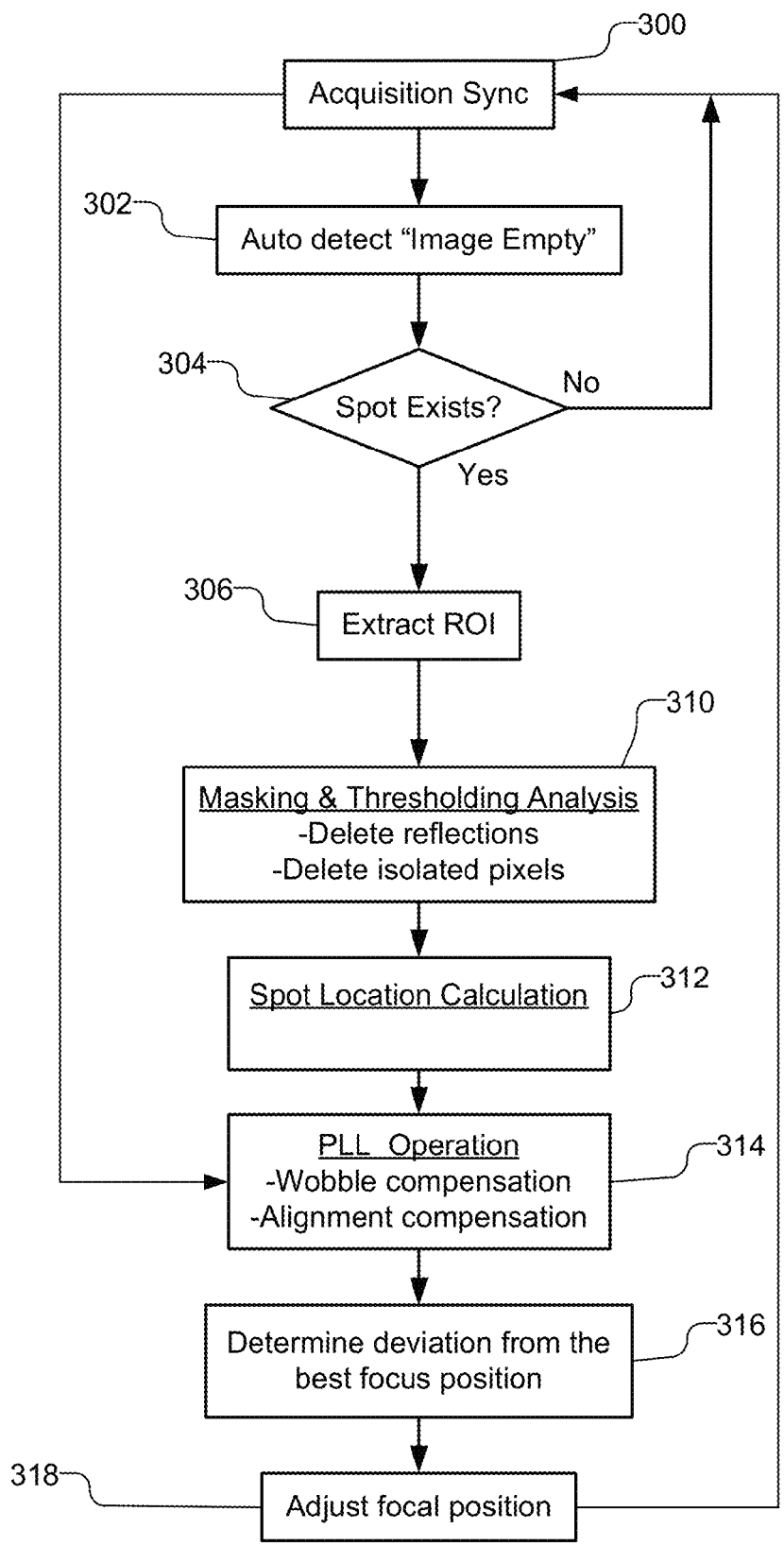
FIG. 4 is a flow chart illustrating processing of the sensor signal provided by the camera to automatically adjust the focal position of the ellipsometer.

FIG. 4 illustrates a flow chart of the auto focus process, which may be performed completely or in part by camera 156 or frame grabber board 157, e.g., (FPGA and DSP), external to the computer 130. As illustrated, an acquisition synchronization 300 step is performed, in which the controller/driver 105D for the rotating compensator 105 (or polarizer 104) provides a synchronization (trigger) signal to the frame grabber board 157 to be used to compensate for spot movement on the sample, as discussed below. An auto detection of an empty image is performed (302). An empty image is detected, e.g., by finding a threshold level to separate the spot from the background by auto thresholding, which well known in the art of image processing. If a spot does not exist (304), i.e., there is no ROI, and the process starts over with acquisition synchronization 300. If a spot does exist (304), the region of interest may be extracted from the image (306). If desired, e.g., where the spot size is as large as the sensor 204 or where the processor is sufficiently powerful, such as when an FPGA is used in the frame grabber board 157, a ROI is not extracted and the whole image is calculated directly.

To extract the ROI (306), the image is summed horizontally (X) and vertically (Y) into vectors and the maximum in both vectors is found in X and Y. Using the maximum in X and Y, the ROI can be located and extracted in the image data. The spot can then be determined from the 2D data of the image in the ROI. Masking and thresholding is then performed (310) to filter noise from the signal. In this step, a histogram showing the number of pixels at a given intensity is produced. Most of the pixels receive little or no signal, so there will be a large peak near zero intensity. The pixels that are illuminated in the auto focus spot will produce a second peak. However, some pixels outside the auto focus spot may be illuminated due to background or scattered light, which are to be removed. To determine if any given pixel is part of the auto focus spot or part of the background, a technique, such as inter class variation auto threshold algorithm, may be employed. The pixels that are part of the auto focus spot are retained, while pixels that are determined to be outside the auto focus spot, e.g., due to reflections or isolated pixels are eliminated or masked.

The spot location calculation for the pixels inside the mask is then performed (312). In one embodiment, the spot location may be determined based on the centroid of the spot. Other techniques, however, may be used to calculate the spot location. For example, the average x, y location of the pixels in the spot may be used to determine a location of a center of the spot, or a smoothing function may be used to smooth the points in the spot and the maximum may be used as the location of the center of the spot. Alternatively, the center of the spot may be found using a large scale optimization problem, e.g., by treating the perimeter of the spot as an ellipse and finding the center of the ellipse. Of course, other techniques or variation of the above may be used if desired. By way of example, the location of the spot may be calculated as a centroid based on the gray level values (or, alternatively, the binary values) of pixels that have an intensity that is greater than the threshold. A simple centroid calculation would be to assume that all of the pixels inside of the mask are weighted equally, i.e., binary centroid calculation. However, it has been found that when the spot has a Gaussian distribution, the brighter pixels near the center of the "blob" of remaining pixels have less noise than the dimmer pixels at the edge of the blob. Accordingly, a grey level centroid may be produced using a centroid calculation that is weighted by the pixel intensity (aka grey scale), where brighter pixels have a stronger weighting in the calculation according to their intensity, which improves the focus precision. The use of a binary centroid calculation, however, may be advantageous when the internal structure of the spot is not homogenous and is changing in correlation to the changes on the wafer patterns. The auto focus system should be insensitive to the wafer pattern so in that case a binary centroid calculation may be used.

A phase locked loop (PLL) operation may be used (314) to synchronize with the angular position of the rotating optics, so that wobble in the rotating optics may be compensated. As discussed above, the controller/driver 105D for the rotating optic (i.e., compensator 105 or polarizer 104) outputs a signal indicating the angular position of the rotating optic, which is acquired during the acquisition synchronization (300) step. Using the angular position signal as a "trigger" signal, a PLL is used to lock on the trigger signal and compensation for any wobble in the rotating optic may be performed using a look up table (LUT) in the FPGA in the camera 156 or frame grabber board 157 (or in computer 130), where the values of the look up table are obtained through a calibration procedure. The system may be calibrated, e.g., using a silicon wafer, where the rotating optic is rotated one or more rotations. The average spot location shift for every trigger angle is determined and loaded into the LUT. Those values will be subtracted from the calculated position base on the current angular position of the rotating optic. Because the wobble is hardware dependent, i.e., a property of the optical components of the ellipsometer, and does not change with alignment, this calibration is not expected to change frequently.

Additionally, with the PLL locked on the synchronization signal from the rotating optics, a LUT may be used (314) to compensate for alignment. The location of the spot on the sensor is calculated based on pixels units and not in nanometer units. The center of the sensor 204, however, might not be perfectly aligned to perfect focus for the ellipsometer. Moreover, motion of the spot on the sensor 204 may not be linear, for example, because the motion of the spot on the sensor 204 is the result of angular motion, while the sensor 204 is linear. Thus, a second LUT may be loaded into memory based on automatic calibration procedure to compensate for linearity, to shift the zero position, and to translate pixels into nanometers. In other words, the alignment LUT is obtained by stepping through the Z axis and comparing the ellipsometer best focus to the spot location on CCD in pixels, which is analyzed and loaded into a LUT so that a spot location in pixels may be input to the LUT and the focus errors in microns or stage encoder counts is output from the LUT.

Figure 5:
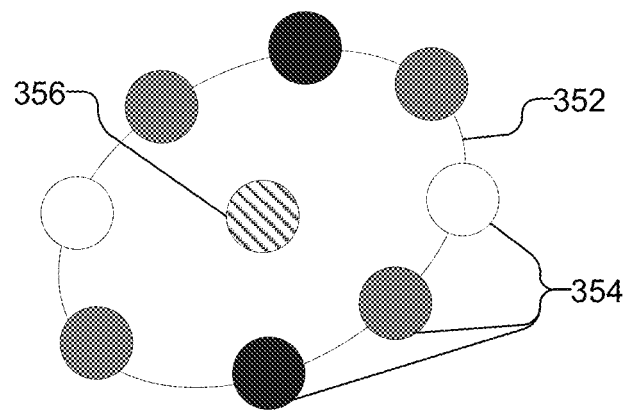
FIG. 5 illustrates movement of the auto focus spot on the sensor due to wobble of the rotating optics.

FIG. 5 illustrates movement of the auto focus spot on the sensor 204 due to the wobble of the rotating optics and the correction of the movement to produce a centered auto focus spot described in step 314. The outer ellipse 352 represents the movement of the illumination spot, where the spots 354 represents a sequence of eight exposures as the rotating optic rotates 360°. The spot location is calculated for every image frame individually and thus, in practice, there are more than eight exposures for 360° rotation of the optics. The different gray levels of the spots 354 represent different intensities. As the rotating optic, e.g., compensator 105, rotates, the focus spot location on the auto focus sensor 204 follows the path of an ellipse, even though the focus has not changed. Thus, the image acquisition is synchronized with the angular position of the rotating optic. The rotating optic hardware may be designed to send, e.g., 13 trigger signals per 360° rotation of the rotating optics. The use of the PLL, as discussed above, permits division the ellipse 352 into any desired number of angles. During calibration, an XY position fix on the sensor 204 is obtained for every desired angular position of the rotating optic. The position fix is stored in the compensation LUT. Spot 356 in FIG. 5 represents the corrected location produced using the PLL operation (314), which is the location of the auto focus spot if the rotating optics had no wobble.

For example, during calibration, the ellipsometer 100 is placed above a blank silicon wafer in that is in focus. The PLL will lock on the triggering signal from the compensator signal and produce camera triggers at the predefined acquisition angles. The camera 156 will capture images at every designated angle (triggering from the PLL logic). By way of example, in FIG. 5, eight acquisition angles are shown, but additional (or fewer) acquisition angles may be used, e.g., 13 angles. The XY offset from the center of the sensor is calculated for each image. The offset is stored in the LUT. At run time, the PLL will subtract the XY offset that corresponds with the current acquisition angle stored in the LUT from the calculated spot location. The acquisition angles are constant and repeatable and handled by the PLL logic. Because the ellipsometer hardware, i.e., the rotating optic, may have a fixed division of angles, e.g., 13, which may not be equally distributed, the PLL may be synchronized to only the first trigger from the rotating optic in every rotation. The PLL may then generate its own triggers for itself and the camera 156 for the desired division of the acquisition angles.

The deviation from a best focus position is then determined based on deviation of the corrected spot (316) to the center of the sensor 204. The focal position of the ellipsometer 100 is adjusted accordingly (318), e.g., by sending the results to a servo controller for the actuator 109 to move the stage 108.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method of focusing an ellipsometer, the method comprising:
   generating radiation;
   polarizing the radiation to produce a sample beam that is incident on and reflected by a sample to produce reflected radiation; and
   focusing the sample beam on the sample comprising:

focusing a portion of the reflected radiation into a spot on a two-dimensional sensor, the portion of the reflected radiation including an entire cross-section of the reflected radiation;

determining a location of the spot on the two-dimensional sensor;

determining a deviation from a best focus position using the location of the spot on the two-dimensional sensor; and adjusting a focal position of the ellipsometer based on the deviation from the best focus position.

2. The method of claim 1, wherein focusing the portion of the reflected radiation into a spot on the two-dimensional sensor provides a magnified indication of at least 2× of any deviation from the best focus position of the ellipsometer and produces the spot that is 50 percent or smaller than the two-dimensional sensor.

3. The method of claim 1, further comprising splitting the portion of the reflected radiation from the reflected radiation and compensating for optical aberrations in the reflected radiation caused by splitting the portion of the reflected radiation.

4. The method of claim 1, wherein determining a location of the spot on the two-dimensional sensor comprises finding a centroid of the spot found.

5. The method of claim 1, wherein the location of the spot with respect to a center of the two-dimensional sensor is mis-aligned with the best focus position of the ellipsometer, the method further comprising compensating for mis-alignment of the location of the spot from the center of the two-dimensional sensor.

6. The method of claim 1, further comprising rotating polarization of the radiation by rotating an optical element that causes the location of the spot on the two-dimensional sensor to move as the optical element rotates, the method further comprising compensating for movement of the location of the spot on the two-dimensional sensor caused by rotation of the optical element.

7. The method of claim 1, further comprising controlling at least one of exposure time and gain for the two dimensional sensor using a proportional-integral-derivative controller.

8. A method of focusing an ellipsometer, the method comprising:

producing a polarized sample beam that is incident on a sample, wherein reflected radiation is reflected by the sample;

splitting a portion of the reflected radiation from the reflected radiation, the portion of the reflected radiation including an entire cross-section of the reflected radiation;

focusing a portion of the reflected radiation into a spot on a two-dimensional sensor;

determining a location of the spot on the two-dimensional sensor;

determining a deviation from a best focus position using the location of the spot on the two-dimensional sensor; and adjusting a focal position of the ellipsometer based on the deviation from the best focus position.

9. The method of claim 8, wherein focusing the portion of the reflected radiation into a spot on the two-dimensional sensor provides a magnified indication of at least 2× of any deviation from the best focus position of the ellipsometer and produces the spot that is 50 percent or smaller than the two-dimensional sensor.

10. The method of claim 8, further comprising compensating for optical aberrations in the reflected radiation caused by splitting the portion of the reflected radiation.

11. The method of claim 8, wherein determining a location of the spot on the two-dimensional sensor comprises finding a centroid of the spot found.

12. The method of claim 8, further comprising rotating polarization of the radiation by rotating an optical element that causes the location of the spot on the two-dimensional sensor to move as the optical element rotates, the method further comprising compensating for movement of the location of the spot on the two-dimensional sensor caused by rotation of the optical element.

13. The method of claim 8, further comprising controlling at least one of exposure time and gain for the two dimensional sensor using a proportional-integral-derivative controller.

14. An ellipsometer comprising:

a source that emits radiation;

a polarization state generator for polarizing the radiation to produce a sample beam that is incident on and reflected by a sample;

a polarization state analyzer positioned to receive reflected radiation from the sample;

a detector positioned to receive the reflected radiation after the reflected radiation passes through the polarization state analyzer; and a focusing system to focus the sample beam on the sample, the focusing system comprising:

a beam splitter in a beam path between the sample and the detector, the beam splitter positioned to receive the reflected radiation and to provide a portion of the reflected radiation that includes an entire cross-section of the reflected radiation;

a lens system that receives the portion of the reflected radiation, the lens system provides a magnified indication of any deviation from a best focus position of the ellipsometer;

a two-dimensional sensor positioned to receive the portion of the reflected radiation from the lens system as a spot, the two-dimensional sensor generates an image signal of the spot;

a processor that receives the image signal and is configured to find a location of the spot on the two-dimensional sensor to determine the deviation from the best focus position of the ellipsometer using the location of the spot on the two dimensional sensor.

15. The ellipsometer of claim 14, wherein the two-dimensional sensor and the lens system in the focusing system produce a spot on the two-dimensional sensor that is 50 percent or smaller than the two-dimensional sensor.

16. The ellipsometer of claim 14, further comprising a compensator positioned in the beam path between the beam splitter and the detector, the compensator correcting optical aberrations in the reflected radiation caused by the beam splitter.

17. The ellipsometer of claim 14, further comprising stage servo controller coupled to the processor and that alters a focal position of the ellipsometer, wherein the stage servo controller alters the focal position of the ellipsometer based on the deviation from the best focus position.

18. The ellipsometer of claim 14, wherein the processor finds the location of the spot based on a centroid of the spot.

19. The ellipsometer of claim 14, wherein the ellipsometer comprises a rotating optic that causes the location of the spot to move on the two-dimensional sensor as the rotating optic rotates, wherein the processor is configured to compensate for movement of the location of the spot on the two-dimensional sensor caused by the rotating optic.

20. The ellipsometer of claim 14, further comprising a proportional-integral-derivative controller coupled to the two-dimensional sensor, the proportional-integral-derivative controller controlling at least one of exposure time and gain for the two-dimensional sensor.

\* \* \* \* \*